United States Patent [19]

Chandrasekaran

[11] Patent Number: 5,673,707
[45] Date of Patent: Oct. 7, 1997

[54] ENHANCED PERFORMANCE GUIDEWIRE

[75] Inventor: V. Chandru Chandrasekaran, Seattle, Wash.

[73] Assignees: Boston Scientific Corporation; Northwest Technology Center, Inc., both of Redmond, Wash.

[21] Appl. No.: 311,568

[22] Filed: Sep. 23, 1994

[51] Int. Cl.⁶ ................................................. A61B 5/00
[52] U.S. Cl. ........................................ 128/772; 128/657
[58] Field of Search ................................ 128/657, 772; 604/164, 170, 280, 282

[56] References Cited

U.S. PATENT DOCUMENTS

| | | |
|---|---|---|
| Re. 34,695 | 8/1994 | Mar et al. ............ 128/772 |
| 3,452,742 | 7/1969 | Muller . |
| 3,503,385 | 3/1970 | Stevens . |
| 3,528,406 | 9/1970 | Jeckel et al. . |
| 3,547,103 | 12/1970 | Cook . |
| 3,625,200 | 12/1971 | Muller . |
| 3,789,841 | 2/1974 | Antoshkiw . |
| 3,906,938 | 9/1975 | Fleischhacker . |
| 3,973,556 | 8/1976 | Fleischhacker . |
| 4,003,369 | 1/1977 | Heilman et al. ....... 128/772 |
| 4,020,829 | 5/1977 | Willson et al. . |
| 4,215,703 | 8/1980 | Willson . |
| 4,538,622 | 9/1985 | Samson et al. . |
| 4,545,390 | 10/1985 | Leary . |
| 4,554,929 | 11/1985 | Samson et al. . |
| 4,619,274 | 10/1986 | Morrison . |
| 4,757,827 | 7/1988 | Buchbinder . |
| 4,846,186 | 7/1989 | Box et al. . |
| 4,854,330 | 8/1989 | Evans, III et al. . |
| 4,984,581 | 1/1991 | Stice . |
| 4,991,602 | 2/1991 | Amplatz et al. ....... 128/772 |
| 5,067,489 | 11/1991 | Lind . |
| 5,234,003 | 8/1993 | Hall . |
| 5,363,847 | 11/1994 | Viera ................... 128/772 X |
| 5,365,942 | 11/1994 | Shank . |
| 5,404,887 | 4/1995 | Prather . |
| 5,429,139 | 7/1995 | Sauter . |

*Primary Examiner*—Sam Rimell
*Attorney, Agent, or Firm*—Cowan, Liebowitz & Latman, P.C.

[57] ABSTRACT

The present invention represents an improved guidewire for use in medical applications designed to cross lesions/stenoses within body cavities and/or blood vessels. The guidewire is provided with a main elongated section of uniform diameter, a tapered section of reduced diameter distal to said main section, and an elongated spring safety core section distal to said tapered section and having a distal end which comprises a short section of enlarged diameter relative to the diameter of the spring core safety section and which forms a blunted tip at the distal end of the guidewire.

18 Claims, 3 Drawing Sheets

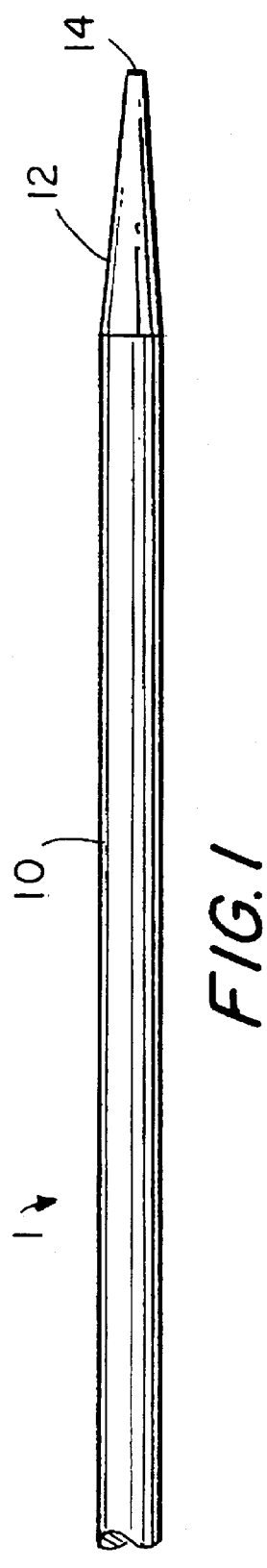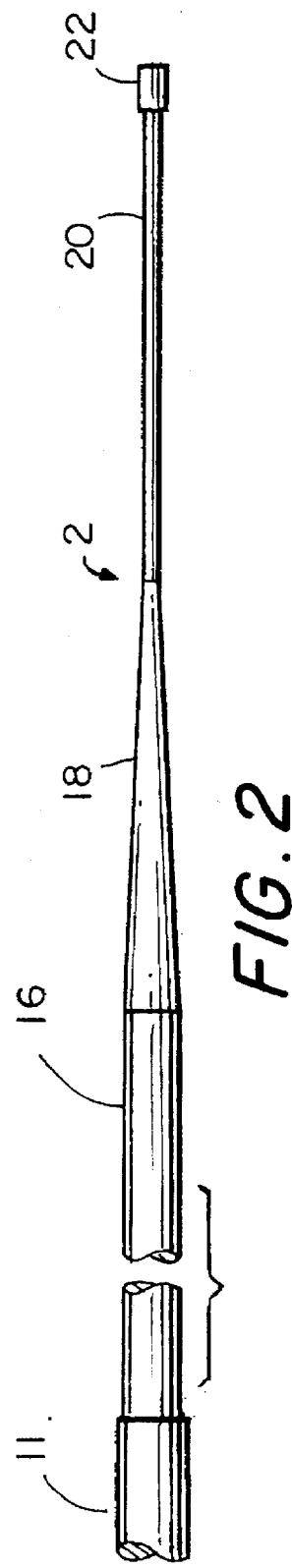

ENHANCED PERFORMANCE GUIDEWIRE

FIELD OF THE INVENTION

This invention relates to guidewires which are useful in medical applications, especially guidewires which are designed to cross lesions/stenoses within body cavities and/or blood vessels. More particularly, the present invention pertains to an improvement in such guidewires whereby these devices are provided with tip designs which enhance the strength, pushability and steerability of the guidewires in various applications.

BACKGROUND OF THE INVENTION

Various prior art devices are known which allow a user to insert a catheter/guidewire means into a body cavity or blood vessel to deliver an inflatable balloon, cutting device or other therapeutic means to a desired site. In carrying out such procedures, which may be generally described as either angioplasty or atherectomy, the object is to effect the opening of a stenotic segment of a blood vessel.

Generally speaking, angioplasty comprises use of an inflatable dilatation balloon positioned in an artery to dilate the artery at a stenosis. A typical angioplasty device is disclosed in, for example, U.S. Pat. No. 4,896,669 to Bhate et al. The angioplasty device of Bhate et al. includes an inflatable balloon which is attached to the distal end of a hollow catheter. The proximal end of the catheter is attached to a fluid source, providing fluid communication between the balloon and the fluid source.

To treat an arterial stenosis, the Bhate et al. balloon is introduced into the artery in a deflated state and guided through the artery over a guidewire to a position adjacent the stenosis. Fluid from a fluid source is then infused into the balloon via the catheter to inflate the balloon. As the balloon expands, it dilates the lumen of the artery. The balloon is then deflated and removed from the artery.

An alternative to angioplasty is an atherectomy procedure which typically includes inserting a guidewire into an affected artery and advancing a cutting device over the guidewire until the cutting device is positioned adjacent to a stenosis. The cutting device is then advanced into the stenosis to cut a channel through the plaque, thereby increasing bloodflow through the artery.

Coil spring guidewires have been widely used for facilitating the insertion of a catheter into a vessel in the body. In some applications a coil spring guidewire with a rounded tip is inserted into a vessel, a catheter is slipped about the coil spring guide until the catheter is in place, and then the guidewire is retracted from the vessel. In another application, a coil spring guidewire is first inserted into a catheter with the rounded tip of the guidewire extending beyond the distal end of the catheter. Then, this assembly is inserted into a vessel with the rounded tip of the coil spring guidewire facilitating placement of the guidewire and catheter tubing in the vessel without additional puncturing of the vessel.

It is desirable in using such guidewires to provide some steering means, such as means for deflecting the tip of the guidewire to facilitate movement of the guidewire around or through a curved path in the vessel. There have been a number of patents directed to different constructions intended to provide a deflectable or flexible tip in a coil spring guidewire. For example, such constructions are set forth in Muller, U.S. Pat. Nos. 3,452,740 and 3,452,742, Stevens, U.S. Pat. No. 3,503,385, Cook, U.S. Pat. No. 3,521,620, Jeckel et al., U.S. Pat. No. 3,528,406, Cook, U.S. Pat. No. 3,547,103, Muller, U.S. Pat. No. 3,625,200, Antoshkiw, U.S. Pat. No. 3,789,841, Tate, U.S. Pat. No. 3,841,308, Fleischhacker, U.S. Pat. No. 3,906,938, Fleischhacker et al., U.S. Pat. No. 3,973,556, Heilman, U.S. Pat. No. 4,003,369, Willson et al., U.S. Pat. No. 4,020,829, Willson, U.S. Pat. No. 4,215,703, Miles, U.S. Pat. No. 4,456,017, Samson et al., U.S. Pat. No. 4,538,622, Leary, U.S. Pat. No. 4,545,390, Samson et al., U.S. Pat. No. 4,554,929, Morrison, U.S. Pat. No. 4,619,274, Crittenden et al., U.S. Pat. No. 4,719,924 and Buchbinder, U.S. Pat. No. 4,757,827, all of which are incorporated herein by reference.

While each of the above-mentioned patents provides guidewires having some steerability or flexibility, there is still a need to develop a guidewire having better steerability and pushability. More particularly, there has been a need to develop a small diameter guidewire wherein its distal tip can be rotated and deflected to impart enhanced steerability and pushability suitable for cardiovascular applications.

Requirements for guidewires used in coronary vascular applications include the following: flexibility, incorporation of an atraumatic and radiopaque spring tip, the ability to form the spring tip to include a curvature, a smooth bend transition proximal to the spring tip, as well as good pushability and steerability to enable quick and safe placement of the guidewire across the lesion. All of the foregoing requirements are applicable for guidewires used with the rotating cutting devices used in atherectomy.

Typically, guidewires used in atherectomy are provided with a platinum spring surrounding the distal end of the core guidewire. The platinum spring is normally welded to the end of the core guidewire to provide the combination of required stiffness and flexibility.

The flexibility of the radiopaque platinum spring tip is dependent on the stiffness of the inner core and the platinum spring. The inner core geometry has a very strong influence on the stiffness of the spring tip. Inner cores with very a small diameter, approaching 0.001", or ribbon cores with a thickness of 0.0005", render the spring tip very soft and flexible.

Attaching these extremely fine core wires to the spring tip is a challenge, whether soldering or micro-welding techniques are employed. Due to the large annular gap between the very fine core wire and the surrounding platinum spring, excess solder tends to wick into the platinum spring. In the case of micro-welding using a plasma arc, the very fine core wire is rapidly consumed in the plasma arc, and often there is no weld between the core and the platinum spring.

Therefore, there is a fundamental problem in effectively joining a very fine core wire to the outer platinum spring. The micro-plasma welding process is preferred because it is quick, can be controlled, requires no fluxes and cleaners, and produces atraumatic hemispherical welds. To successfully adapt the micro-plasma welding process to weld very fine core wires to platinum springs, the geometry of the core wire tip must, therefore, be modified for low melting point materials such as stainless steel. For refractory metal wires such as tungsten and molybdenum, modification of the core wire tip may not always be necessary but is still desirable for other reasons.

The guidewires most commonly used in interventional cardiology include 0.014 and 0.018 inch diameter wires. When such larger wire diameters are used, it is relatively simple to design and produce guidewires with good pushability and steerability. The pushability and steerability are determined by the efficiency with which push/pull forces and torque are transmitted from the proximal end, outside the patient, to the distal tip inside the coronaries. This efficiency factor is controlled by the torsional stiffness of the wire and varies in relation to the fourth power of the diameter. The design and manufacturing challenges increase considerably as the wires become smaller in diameter.

The commercially available 0.014 and 0.018 inch diameter guidewires utilize a long stainless steel spring, typically 10 inches or more, wound around the distal portion of the core wire and secured adjacent to the radiopaque spring tip. The purpose of this long stainless steel spring is to improve the pushability and steerability of the guidewire. However, a guidewire with such a long coil construction has limited usefulness in conjunction with certain rotational atherectomy devices. For example, the trifilar drive shaft of the ROTABLATOR® atherectomy device, available from Heart Technology, Inc., of Redmond, Wash., is typically operated at from about 150,000 to 200,000 rpm during an atherectomy procedure. The guidewire with a long coil construction does not function reliably with the ROTABLATOR device, apparently due to entanglement of the trifilar drive shaft and the long coil secured to the guidewire.

OBJECTS OF THE INVENTION

It is, therefore, an object of the present invention to provide an improved guidewire whereby the guide wire tip is provided with a configuration which more easily allows the user to move the guidewire through a stenotic segment of a blood vessel.

It is another object of the present invention to provide a guidewire having a tip configuration which significantly increases the strength of the distal joint between the core wire and the surrounding platinum spring.

It is a further object of the present invention to provide an improved guidewire with a maximum shaft diameter of 0.009 inches having a short radiopaque spring surrounding the distal end, but without the long secondary stainless steel coil, and yet provide enhanced flexibility, pushability, and steerability to such a guidewire over that presently available using prior art configurations.

These and other objects of the invention will become apparent from the following description of the invention.

SUMMARY OF THE INVENTION

In the present invention, the enhanced performance is achieved without the use of a long coil. The 0.009 inches diameter guidewire is dictated by the size of the burr opening in the ROTABLATOR catheter. The guidewire is a monofilament construction to provide reliable and repeatable operation with the ROTABLATOR. The guidewire is centerless ground with a complex profile over the distal 18 inches to modulate the stiffness and thereby significantly enhance the pushability, steerability and also enable the burr to track the form of the guidewire in the coronaries. The enhanced performance guidewire in this invention can be used in PTCRA, PTCA and other transluminal applications.

The present invention provides for an improved guidewire for use in medical applications designed to cross lesions/ stenoses within body cavities and/or blood vessels. The guidewires are provided with tip designs which enhance the pushability and steerability of the guidewires when they are used in various applications.

Additionally, the present invention provides for an improved guidewire configuration wherein the tip of the guidewire core is provided with a series of tapers and cylindrical sections. These tapers and cylindrical sections enhance the pushability and steerability of the guidewires to allow the guidewires to more effectively cross lesions/ stenoses within body cavities and/or blood vessels.

Further, the present invention provides a guidewire having a spring surrounding the distal end of the guidewire, which spring is joined to the tip of the guidewire. The joined guidewire and surrounding spring arrangement possess enhanced strength over conventionally joined guidewire spring arrangements due to the design of the tip of the guidewire. This design provides an enhanced area for joining said guidewire and spring.

BRIEF DESCRIPTION OF THE DRAWINGS

FIG. 1 is a schematic representation of a typical prior art guidewire core wire;

FIG. 2 is a schematic representation of one embodiment of a guidewire core wire according to the present invention;

DETAILED DESCRIPTION OF THE INVENTION

Figure 3:
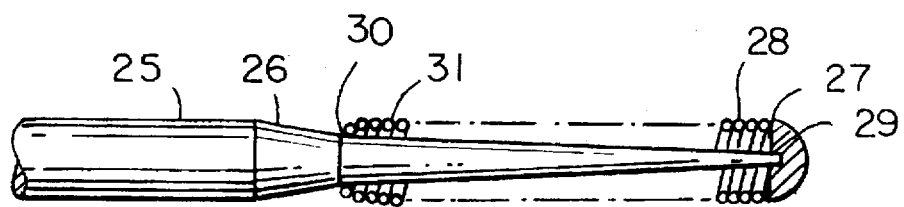
FIG. 3 is a schematic representation of a prior art guidewire tip with a spring.

The present invention provides for improved guidewires for use in medical applications designed to cross lesions/ stenoses within body cavities and/or blood vessels. The guidewires are provided with tip designs which enhance the pushability and steerability of the guidewire when used in various applications.

The improved guidewire configuration of the present invention incorporates a novel design wherein the guidewire comprises a core wire comprising tapers and cylindrical sections and whose tip is blunted or flattened. This design serves to enhance both the pushability and steerability of the guidewire, which permits the user to more effectively cross lesions/stenoses. The blunted or flattened end improves the ability to bond a distal spring to the core wire.

In a preferred embodiment of the present invention the guidewire has a spring surrounding the distal end of the core wire where the spring is joined to the blunted or flattened end of the core wire tip. This allows a more effective joining which imparts improved strength to the joined core wire and spring arrangement due to the enhanced area provided by the blunted or flattened end whereby the said spring may be more effectively welded to the tip of the core wire.

The construction and obvious advantages of the improved guidewire provided for in the present invention will be more clearly understood from the following description of various specific embodiments set forth in the accompanying drawings. FIG. 1 is a schematic representation of a typical known core wire 1 for a guidewire. The core wire 1 consists of a main elongated body 10 of varying length having a tapered section 12 which terminates at the distal end 14 of the core wire 1.

For a core wire useful in a guidewire for an atherectomy device such as the ROTABLATOR® atherectomy device sold by Heart Technology, Inc. of Redmond, Wash., the overall diameter of the main elongated body 10 of the core wire 1 of FIG. 1 will be approximately 0.009 inches. The tapered section 12 will be approximately 1.6 inches in overall length and will terminate in end 14, which is approximately 0.0022 inches in diameter.

FIG. 2 is a schematic representation of an embodiment of a core wire according to the present invention. The core wire 2 has a compound grind over approximately 18 inches of the distal portion thereof immediately adjacent to the generally elongated main body 11. Main body 11 is attached to a reduced section 16, which is in turn attached to a tapered transition section 18. Section 18 is attached to a spring safety core section 20, which terminates at its distal end in a short section of enlarged diameter which forms blunted tip 22.

Figure 6:
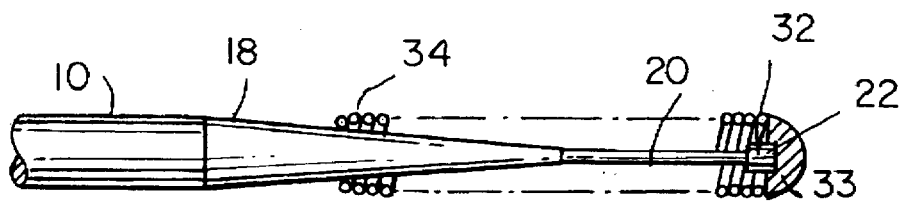
FIG. 6 is a schematic representation of an embodiment of a guidewire tip with a spring according to the present invention.

The spring safety core section 20 of the core wire depicted in FIG. 2 is preferably of uniform cross-section, typically from about 0.0014 to 0.0025 inches in diameter, and is very flexible. Optionally the cross-section of spring safety core section 20 could be rectangular, indicating a "flat" safety core section, or even square or oval, of similar dimensions. To ensure a smooth bend radius proximal to the spring safety core section 20, the guidewire has a transition section 18 which is from about 2 to 10 inches long, preferably about 5 inches long, and has a gradual taper. In the absence of a transition section, a highly flexible spring around the core wire, as shown in FIG. 6, would be prone to bend abruptly around tight corners in a patient's coronaries with the likelihood of kinking and/or failure of the guidewire.

The reduced section 16 of the core wire is typically from about 8 to 16 inches long, preferably about 12 inches long and has a uniform cylindrical cross-section of from about 0.006 to 0.008 inches in diameter. The reduced section 16 is preferably incorporated as a continuous piece with body 11 to avoid any potential problem associated with having the nature of the core wire material differ from that of the reduced section. The core wire is preferably fabricated from ultra high strength stainless steel wire, straightened and cut to length. Alternatively useful core wire materials include nitinol, titanium, and nickel and/or cobalt base alloys. It is within the scope of the invention that different sections of the core wire could be comprised of different materials or that two or more of the materials described could be combined.

With reference to FIG. 3, a conventional guidewire tip is depicted showing the distal end of the main elongated body 25 and a tapered section 26 terminating at the distal end of the taper 27. A coiled spring 28 surrounds tapered section 26, and there is a joining weld 29 between the tip of the core wire and the distal end of the spring 28, as well as the joining weld 30 between the tapered section 26 and the proximal end 31 of the spring 28. The typical tapered core bare guidewire of FIG. 3 will generally terminate in a tip having a diameter of from about 0.001 to 0.0018 inches.

Problems associated with fabricating a reliable spring tipped guidewire as depicted in FIG. 3 lie in the difficulty of obtaining a good weld between the end of the spring and the tip due to vaporizing and softening of the fine diameter core guidewire in the presence of the plasma arc generally employed in the welding process. To overcome such problems, and to provide a greater surface for welding the end of the spring tip to the bare guidewire, various other guidewire tip arrangements according to the present invention are shown.

Figure 4:
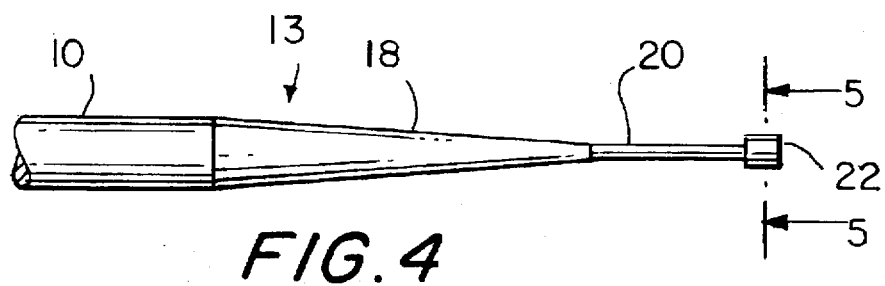
FIG. 4 is a partial detail of the embodiment of the present invention shown in FIG. 2.
Figure 5:
FIG. 5 is a perpendicular cross-sectional view of the distal portion of the embodiment of the invention shown in FIGS. 2 and 4.

FIG. 4 is a detail of FIG. 2, showing a modified core guidewire tip which terminates in a larger diameter section 22 rather than in a sharp point 12 as depicted in FIG. 3. The diameter of section 22 will be from about 0.003 to 0.005 inches, and the length of this section will be from about 0.025 to 0.100 inches. A longitudinal cross-sectional view of the distal section 22 is shown in FIG. 5.

In FIG. 6 a welded spring and core guidewire tip according to the present invention is depicted showing an elongated main body of the guidewire 10, a tapered section 18, and a spring 32 surrounding the elongated safety core section 20 which terminates in the enlarged tip section 22. The location of the joining weld 33 between the enlarged tip section of the guidewire core 22 and the distal end of the spring 32 is shown, as is the location of the joining weld 34 between the proximal end of the spring and the tapered section 18.

The tensile breaking load for the welded spring/guidewire assembly shown in FIG. 6 has been found to be 2 to 3 times higher than the tensile breaking load for the welded spring/guidewire assembly shown in FIG. 3. The weld strengths associated with the welded guidewire/spring tip shown in FIG. 6 are also in a much tighter band, which is also very desirable.

While the guidewire tip arrangement depicted in FIG. 4 is integral with the taper and produced by centerless grinding, other preferred embodiments of such an arrangement are also contemplated.

Figure 7:
FIGS. 7, 8, and 9 are each a schematic representation of an alternative embodiment of a core wire tip according to the present invention.

FIG. 7 is a schematic representation of an alternative embodiment of a guidewire tip, showing the elongated body 10 and the tapered section 18. The elongated safety core section 20 terminates in a short length of stainless steel hypo tube 35 which is oriented coaxially over the distal end of the safety core section 20.

Figure 8:
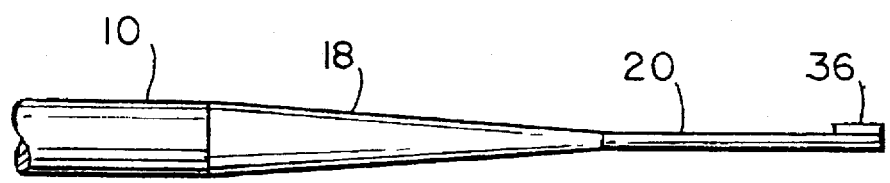

FIG. 8 depicts another alternative embodiment of a guidewire tip according to the present invention showing the main elongated body 10, the tapered section 18, and the safety core section 20 having attached thereto a short section of thin stainless steel ribbon stock 36. In this embodiment a short length of stainless steel ribbon stock is attached to one face of the core wire distal tip. The attachment is accomplished by, for example, use of resistance welding. The modified tip can be welded to a platinum spring to form an assembly as shown similar to that in FIG. 6.

Figure 9:

Another alternative embodiment of the guidewire according to the present invention is depicted in FIG. 9, which shows the main elongated body 10, the tapered section 18, and the safety core section 20 terminating in a tapered tip 36. The tapered tip 37 has a starting diameter at the point of contact with the elongated safety core section 20 which is the same diameter as that of the safety core section and gradually enlarges to a diameter of from about 0.0025 to 0.005 inches. The overall length of the tapered tip section will be from approximately 0.050 to 0.100 inches.

As the guidewire is placed through the tortuosity of the coronaries, the wire will seek to straighten and assume a minimum strain energy configuration. In its attempt to straighten out, the wire will exert forces on the walls of the guide catheter which it may be used as well as on the coronary vessels. These side wall forces in turn contribute to frictional forces which must be overcome to advance the wire axially.

Steering the guidewire requires that the spring tip can be easily re-oriented, or rotated, by the application of torque to the wire external to the patient. The side loads and frictional forces, discussed above, will restrict the transmission of torque from a location external to the patient to the tip placed in a patient coronaries. To reduce the side loads and frictional forces on the guidewire of the present invention, the stiffness of the wire is decreased in the reduced section 16. The reduced section of the guidewire has a smaller diameter than the starting wire, and will be 0.006 to 0.008 inches in diameter over a length of approximately 12 inches. The generally elongated body 10 of the guidewire depicted is typically 0.009 inches in diameter. Shortening the reduced section 16 by 30% or more will reduce the steerability and pushability of the guidewire.

It is contemplated that there will be an optimum balance between the length and diameter of the reduced section 16. This combination will be dependent upon the actual materials and method of construction of the guidewire, which is well within the ability of one skilled in this art to determine. While the reduced section 16 as depicted in FIG. 2 is a uniform cylinder produced by centerless grinding. An alternative to the uniform diameter cylinder design contemplated is a series of stepped cylinders or tapers which progressively reduce the side loads and frictional forces on the guidewire and further improves the pushability and steerability.

It will be further apparent to one skilled in this art that the improvements provided for in the present invention, while described with relation to certain specific physical embodiments, also lend themselves to being applied in other physical arrangements not specifically provided for herein, which are, nonetheless, within the spirit and scope of the invention taught here.

I claim:

1. A guidewire for use in medical applications, which comprises:

a main elongated section of uniform diameter, a tapered section of reduced diameter distal to said main section, a separate elongated spring safety core section welded to the end of said tapered section and which comprises a short section of uniform enlarged diameter relative to the diameter of the spring core safety section and which forms a blunted tip at the distal end of the guidewire, and a spring surrounding the elongated safety core section, said spring having a distal end joined to the enlarged tip at a weld and a proximal end joined to the tapered section.

2. A guidewire according to claim 1, wherein the main elongated section of the guidewire has a diameter of approximately 0.009 inches.

3. A guidewire according to claim 1, wherein the tapered section is approximately 5 inches long.

4. A guidewire according to claim 1, wherein the spring safety core section is from about 0.0010 to 0.0025 inches in diameter.

5. A guidewire according to claim 1, wherein the portion of the spring safety core section proximal to the enlarged distal end has a flat, ribbon-like shape.

6. A guidewire according to claim 1, wherein the guidewire terminates at the distal end in a cylindrical blunt section having an overall length of approximately 0.025 to 0.100 inches.

7. A guidewire according to claim 1, wherein the distal end of the spring is welded to the distal end of the enlarged tip section.

8. A guidewire according to claim 1, wherein the proximal end of the spring is welded or soldered to the tapered section.

9. A guidewire according to claim 1, wherein the elongated safety core section terminates in a short length of stainless steel hypo tube which is oriented coaxially over the distal end of the safety core section.

10. A guidewire according to claim 9, wherein the elongated safety core section is surrounded by a spring joined to the distal end of the stainless steel hypo tube.

11. A guidewire according to claim 1, wherein the elongated safety core section has attached thereto a short section of thin stainless steel ribbon stock.

12. A guidewire according to claim 11, wherein the elongated safety core section is surrounded by a spring joined to the distal end of the thin stainless steel ribbon stock.

13. A guidewire according to claim 1, wherein the elongated safety core section is attached to the distal end of the enlarged tapered section.

14. A guidewire according to claim 1, wherein the enlarged tapered section has an overall length of from about 0.050 to 0.100 inches and enlarges to a diameter of from about 0.0025 to 0.005.

15. A guidewire according to claim 1 which also comprises a reduced diameter section distal to a main elongated section and proximal to the tapered section, which reduced section is of uniform cross-section and which diameter is smaller than the diameter of the main elongated section of the guidewire.

16. A guidewire according to claim 15, wherein the reduced section has a uniform cylindrical cross section having a diameter of from about 0.006 to 0.008 inches.

17. A guidewire according to claim 15, wherein the reduced section is from about 10 to 12 inches in length.

18. A guidewire according to claim 15, wherein the reduced section has an overall length of approximately 12 inches and is comprised of two or more cylindrical or tapered members of increasingly smaller diameter.

* * * * *